United States Patent
Burman et al.

(10) Patent No.: US 6,632,832 B1
(45) Date of Patent: Oct. 14, 2003

(54) ANTI-CANCER ACTIVITY OF CARVEDILOL AND ITS ISOMERS

(75) Inventors: Anand C. Burman, Ghaziabad (IN); Rama Mukherjee, Ghaziabad (IN); Manu Jaggi, Ghaziabad (IN); Anu T. Singh, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 10/238,992

(22) Filed: Sep. 10, 2002

(51) Int. Cl.⁷ .............................................. A61K 31/40
(52) U.S. Cl. .................. 514/411; 514/908; 436/64; 436/813; 435/366; 435/371; 435/372.1; 435/377
(58) Field of Search ................................ 514/411, 908; 436/64, 813; 435/366, 371, 372.1, 377

(56) References Cited

U.S. PATENT DOCUMENTS

| | | | |
|---|---|---|---|
| 4,369,326 A | 1/1983 | Petitpierre et al. | 548/418 |
| 4,503,067 A | 3/1985 | Wiedemann et al. | 514/411 |
| 5,399,581 A | 3/1995 | Laragh | 514/396 |
| 5,902,821 A | 5/1999 | Lukas-Laskey et al. | 514/411 |
| 6,096,777 A | 8/2000 | Feuerstein et al. | 514/411 |

OTHER PUBLICATIONS

Jonsson, O.E. et al. "Perivascular Cell Protection *In Vitro* and Increased Cell Survival *In Vitro* by the Antihypertensive Agent Carvedilol Following Radiation", *European J. of Cancer*, (1999), 35(8): 1268–1273.

Sung, Cheng–Po et al. "Carvedilol Inhibits Vascular Smooth Muscle Cell Proliferation", *J. of Cardiovascular Pharmacology*, (1993), 21(2); 221–227.

Lotze, Ulrich et al. "Carvedilol Inhibits Platelet–Derived Growth Factor–Induced Signal Transduction in Human Cardiac Fibroblasts", *J. of Cardiovascular Pharmacology*, (Apr. 2002), 39(4): 576–589.

*Primary Examiner*—Frederick Krass
(74) *Attorney, Agent, or Firm*—Ladas and Parry

(57) ABSTRACT

The present invention provides for pharmaceutical compositions comprising carvedilol for treatment of cancer. More particularly the invention relates to the use of carvedilol for treatment of cancers of the colon, ovary, breast, prostate, pancreas, lung, melanoma, glioblastoma, oral cancer and leukemias. Although not bound to any theory, the anticancer activity of carvedilol appears to be attributed to the inhibition of Epidermal Growth Factor and Platelet derived growth factor dependent proliferation of cancer cells. Further, carvedilol exerts anticancer effect by inhibition of the Protein kinase C (PKC) activity and that of the cyclooxygenase 2 enzyme. The invention also relates to the anticancer activity of the optically pure isomers S(−) and R(+) of carvedilol and the use of carvedilol and its isomers in pharmaceutical compositions for the treatment of cancer.

33 Claims, 6 Drawing Sheets

ANTI-CANCER ACTIVITY OF CARVEDILOL AND ITS ISOMERS

FIELD OF THE INVENTION

The present invention provides for pharmaceutical compositions comprising carvedilol for treatment of cancer. More particularly the invention relates to the use of carvedilol for treatment of cancers of the colon, ovary, breast, prostate, pancreas, lung, melanoma, glioblastoma, oral cancer and leukemias. Although not bound to any theory, the anticancer activity of carvedilol appears to be attributed to the inhibition of Epidermal Growth Factor and Platelet derived growth factor dependent proliferation of cancer cells. Further, carvedilol exerts anticancer effect by inhibition of the Protein kinase C (PKC) activity and that of the cyclooxygenase 2 enzyme. The invention also relates to the anticancer activity of the optically pure isomers S(−) and R(+) of carvedilol and the use of carvedilol and its isomers in pharmaceutical compositions for the treatment of cancer.

BACKGROUND OF THE INVENTION

Carvedilol is a nonselective α-adrenergic blocking agent with β-adrenoreceptor blocking activity. (±)-1-(carbazol-4-yloxy)-3-[(2-(o-methoxyphenoxy)ethyl]amino]-2-propanol, better known as 'carvedilol' has the structural formula shown in FIG. 1. It is a racemic mixture. Carvedilol is a white to off-white powder with a molecular weight of 406.5, represented by the molecular formula $C_{24}H_{26}N_2O_4$. Carvedilol is a racemic mixture in which the S(−) enantiomer exhibits nonselective β-adrenoreceptor blocking activity and both R(+) and S(−) enantiomers at equal potency exhibit α-adrenergic blocking activity. Carvedilol has no intrinsic sympathomimetic activity.

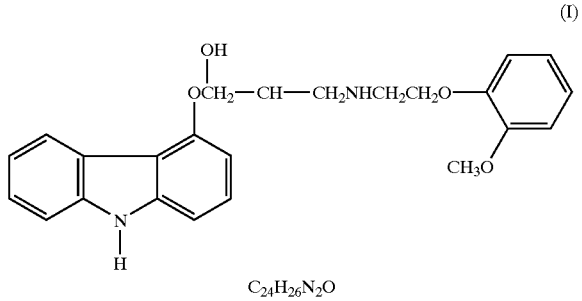

$C_{24}H_{26}N_2O$

Carvedilol is rapidly and extensively absorbed following oral administration due to a significant degree of first-pass metabolism. Following oral administration, the apparent mean terminal elimination half-life of carvedilol generally ranges from 7 to 10 hours. Carvedilol is extensively metabolized. Carvedilol is metabolized primarily by aromatic ring oxidation and glucuronidation. The oxidative metabolites are further metabolized by conjugation via glucuronidation and sulfation. The metabolites of carvedilol are excreted primarily via the bile into the faeces. Demethylation and hydroxylation at the phenol ring produce three active metabolites with β-receptor blocking activity. Based on preclinical studies, the 4'-hydroxyphenyl metabolite is approximately 13 times more potent than carvedilol for β-blockade. Compared to carvedilol, the three active metabolites exhibit weak vasodilating activity. (12000 Mosby's GenRx, the complete reference for Generic and Brand Drugs, Carvedilol (003267)).

Carvedilol is indicated for the treatment of mild or moderate heart failure of ischemic or cardiomyopathic origin, in conjunction with digitalis, diuretics, and ACE inhibitor, to reduce the progression of disease as evidenced by cardiovascular death, cardiovascular hospitalization, or the need to adjust other heart failure medications. Carvedilol may be used in patients unable to tolerate an ACE inhibitor. Carvedilol may be used in patients who are or are not receiving digitalis, hydralazine or nitrate therapy. Carvedilol is also indicated for the management of essential hypertension. It can be used alone or in combination with other antihypertensive agents, especially thiazide-type diuretics.

Carvedilol, is an antihypertensive drug with activity on α-adrenoceptors as well as calcium channel activity. Use of carvedilol in compositions for treatment of congestive heart failure is disclosed in U.S. Pat. Nos. 4,503,067 and 5,902,82. U.S. Pat. No. 4,369,326 discloses carbazolylmethane compounds useful as pressure sensitive or heat recording material. Also carvedilol has been explored for treatment of sexual impotence (U.S. Pat. No. 5,399,581). U.S. Pat. No. 6,096,777 provides a new method for inhibiting the expression of Fas-mediated apoptosis using compounds which are dual non-selective β-adrenoceptor and $α_1$-adrenoceptor antagonists such as carvedilol.

Carvedilol is reported to be a neurohumoral antagonist with multiple actions. Essentially a nonselective adrenergic receptor blocking agent, it has diverse reported properties viz. antioxidant and radical scavenging properties. It inhibits Mitogen activated protein kinase, a key serine/threonine kinase and cell cycle progression in vascular smooth muscle cells. (Sung etal, Pharmacology and Experimental therapeutics, Vol 283, Issue 2, 910–917, 1997).

The cellular signaling routes connecting the GPCRs to the Ras/MAPK pathway have known to involve Tyrosine kinases, PI3 kinases and/or PKC (Gutkind et al., J. Biol Chem, 273,1839–1842, 1998). The ligand independent activation (transactivation) of receptor Tyrosine kinases viz. EGFR, as a key cellular event in the activation of MAPK by specific G protein coupled receptors is also reported (Daub etal, EMBO J. 16, 7032–7044, 1997, Daub etal, Nature,379, 557–560,1996). GPCR activation of Protein kinase C leading to EGFR transactivation and downstream MAPK activation, may be PKC mediated (Tsai etal, EMBO J, 16: 4597–4605, 1997), PKC prevented (Li X etal EMBO J, 17: 2574–2583, 1998), or PKC independent (Daub et al., EMBO J, 16, 7032–7044, 1997, Daub etal , Nature,379, 557–560, 1996.

Tumor cells are well documented to produce autocrine and/or paracrine growth factors which can include platelet derived growth factor (PDGF), epidermal growth factor (EGF), transforming growth factor ∝ (TGF∝), colony stimulating growth factor 1(CSF-1), and fibroblast growth factor (FGF). Growth factors regulate cell growth by activating multiple intracellular signal transduction pathways after binding to high affinity Tyrosine kinase receptors to the cell surface.

Protein kinase C (PKC) is a family of closely related lipid dependent and diacylglycerol activated isoenzymes, with an important role in mitogenesis and tumor promotion. Sustained activation of PKC activity in vivo plays a critical role in regulation of proliferation and tumorigenesis (Blobe et al., Regulation of Protein kinase C and role in Cancer Biology, Cancer Metastasis Rev. 13 (3–4): 411–431, Dec. 13, 1994).

Acquired resistance to chemotherapy is a major problem during cancer treatment. One mechanism for drug resistance is overexpression of the MDR1 (multidrug resistance) gene encoding for the transmembrane efflux pump, P-glycoprotein (P-gp). Carvedilol influences doxorubicin (Dox) cytotoxicity and P-gp activity in a P-gp-expressing cell line compared to a non-expressing subline. Carvedilol reduced P-gp activity approximately twice as effectively as verapamil at an equimolar concentration. This suggests that carvedilol has the clinical potential to reverse tumour MDR involving the efflux protein P-gp.

OBJECT OF THE INVENTION

The invention involves methods for treating various types of cancer in patients using carvedilol or its optically pure isomers.

SUMMARY OF THE INVENTION

The present invention provides pharmaceutical compositions containing carvedilol or its optically pure isomers useful in the treatment of cancer. In particular, the invention provides novel method for treating, inhibiting and/or preventing tumor growth or cancer growth.

Based on the multiple actions of Carvedilol, a study was undertaken to investigate the use of carvedilol for treatment of cancer. It was found by the inventors that carvedilol caused cytotoxicity on different human tumor cell lines depending on the dosage and cell-line used. Carvedilol was separated into its optically pure isomers S(−) and R(+) to determine their use as anticancer agents. The underlying cellular mechanism(s) that may be determining of the observed anticancer effects were investigated.

The effect(s) of Carvedilol on Growth factor dependent mitogenic signaling in cancer cells was investigated. In the context of documented cross talk between the signaling intermediates of G protein coupled receptors and the Tyrosine kinase receptors, the effects of Carvedilol on PKC and PI3 kinase activity was investigated. The effect of Carvedilol on the activity of Cyclooxygenase 2 enzyme and its regulation by selected upstream mediators of these two pathways was also investigated.

DETAILED DESCRIPTION OF THE INVENTION

Figure 1:
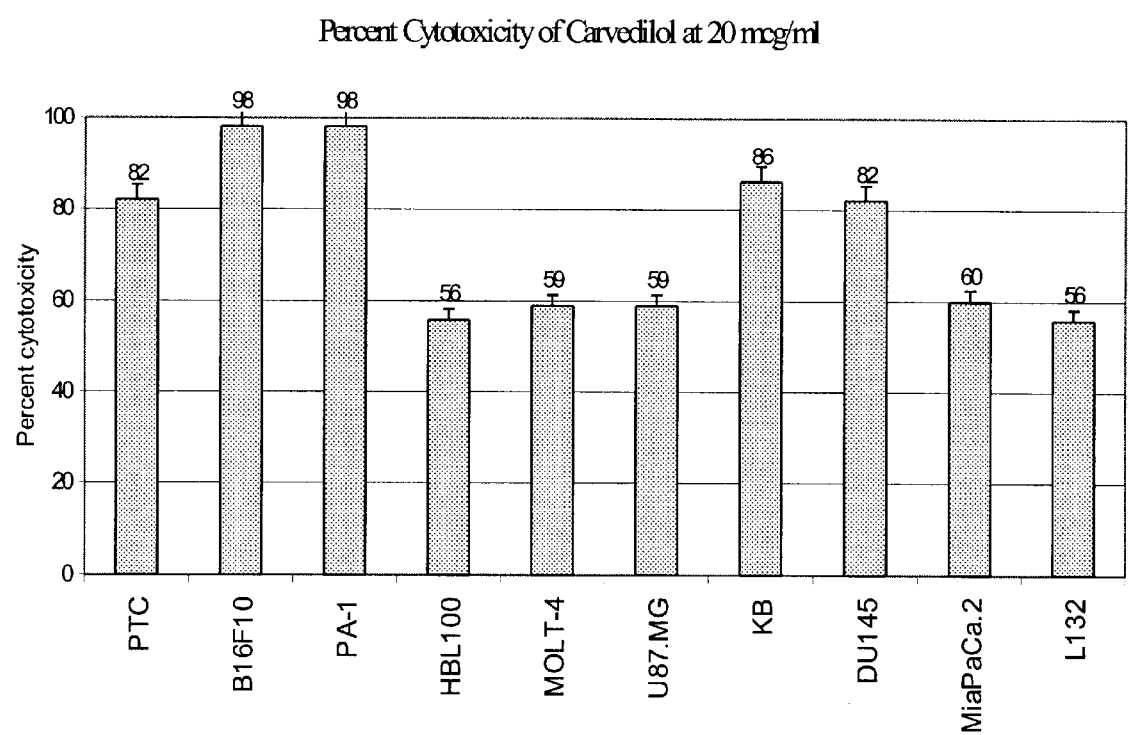
FIG. 1 shows the percent cytotoxicity of carvedilol at 20 mcg/ml.

Carvedilol and its optically pure isomers were tested in various cell lines for their cytotoxic activity and it was found that these compounds can effectively be used for inhibition of tumors and cancer and for treatment of cancer or tumor. Such indications exhibited by these compounds are surprising as carvedilol is generally known to act as an antihypertensive drug and cytotoxic activity is not expected. The modulation of Growth factor dependent proliferation as well as Protein kinase C, a key signaling intermediate involved in cross talk of G protein coupled signaling and receptor tyrosine kinases explained the observed anticancer effects of the molecule.

Pharmaceutical compositions containing an effective amount of the compounds of the invention as described herein above may be prepared according to methods known in the art. By "effective amount", the applicants intend an amount that will produce tumor or cancer inhibiting effects or anti-cancer or anti-tumor effects without causing undue harmful side effects. The pharmaceutical compositions may provide from about 10 mg to 1000 mg of carvedilol or its isomers, per unit dose. The actual dosage for humans and animals will vary depending upon the body weight of the subject, stage of affliction etc. The composition may be administered either alone or as a mixture with other therapeutic agents.

The compositions may be formulated in various physical forms suitable for administration such as tablets, capsules, solutions, injectables, lozenges, powders, aqueous or oily suspensions, syrups, elixirs, implants or aqueous solutions etc.

The compositions containing carvedilol or an optically pure isomer thereof as active ingredients, may be formulated as tablets, if intended for oral use, or lyophilized powders for parenteral administration. The powders may be reconstituted by adding suitable diluents or pharmaceutically acceptable carriers prior to use.

Tablets containing carvedilol or an optically pure isomer thereof as active ingredient may include, along with non-toxic pharmaceutically acceptable excipients. Such excepients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques.

Compositions for oral use may also be presented as hard gelatin capsules wherein the active ingredient comprises carvedilol or an isomer thereof mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The pharmaceutical compositions may also be formulated as solutions, when intended for systemic or parenteral administration. Systemic administration refers to oral, rectal, nasal, transdermal and parentral (i.e., intramuscular, intraperitoneal, subcutaneous or intravenous). The liquid formulation is generally buffered, isotonic or aqueous solution. Examples of suitable diluents are normal isotonic saline solution, standard 5% dextrose in water or buffered sodium or ammonium acetate solution. Formulations suitable for parenteral administration, may also be used for oral administration or contained in a metered dose inhaler or nebulizer. It may be desirable to add excipients such as ethanol, polyvinylpyrrolidone, gelatin, hydroxy cellulose, acacia, polyethylene glycol, mannitol, sodium chloride or sodium citrate.

Alternatively, the compounds of the invention may be prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit.

The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The compositions may contain additives selected from the group consisting of sweetening agents, flavoring agents, coloring agents and preserving agents.

The nature of pharmaceutical composition employed will, of course, depend on the desired route of administration.

The present invention provides for method(s) for the treatment of cancer or tumors, said method comprising the steps of administering to the subject an effective amount of carvedilol or an isomer thereof to a patient in need thereof.

The present invention provides for method(s) for the inhibition of cancer or tumors, said method comprising the steps of administering to the subject an effective amount of carvedilol or an isomer thereof to a patient in need thereof. An effective amount of carvedilol or an isomer thereof is an amount sufficient to treat the cancer or tumor or inhibit the growth and/or replication of the cancer or tumor. The patient can be human, mammal or other animal.

The dosage in human beings for treatment of cancer or a tumor or inhibition of tumor or cancer includes the active ingredient (carvedilol or an isomer thereof) in combination with conventional pharmaceutical agents. The usual dosage is about 3 to 30 g of active ingredient as a single dose or divided doses. The preferred and actual dosage will be determined according to the specific compositions formulated, mode of administration, the site of administration and the patient being treated.

No unexpected or toxic effects were observed when the compounds of the invention were tested for treatment of cancer or tumors or inhibition of tumors or cancer.

The invention is further described in detail by the following examples which are given for illustration of the invention and not intended to limit the scope thereof in any manner.

EXAMPLE 1

In vitro Cytotoxicity and Anti-cancer Spectrum of Carvedilol

In vitro cytotoxic activity of carvedilol and its isomers was determined by performing the MTT cytotoxicity assay (Mosmann T., J Immunological Methods, 65:55; 1983). Briefly, the cultured tumor cells were separately seeded in a 96-well culture plate and co-incubated with carvedilol or its isomers dissolved in methanol, dimethyl formamide, dimethyl sulfoxide or isopropyl alcohol with relevant controls at 37° C. in a $CO_2$ incubator. After 72 hours, the assay was terminated and percent cyotoxicities calculated. As shown in Table 1, Carvedilol shows good in vitro cytotoxicity in Human Colon, Ovary, melanoma, Leukemia, Glioblastoma, Prostate, oral and Lung tumor cell lines with $ED_{50}$ values less than 20 μg/ml. These results demonstrate that Carvedilol is a potential anti-cancer agent with broad-spectrum anti-cancer activity. Further, FIG. 1 shows the high cytotoxicity effect of carvedilol on all of the above-mentioned tumor cell lines, except oral, at a fixed concentration of 20 μg/ml.

| IN VITRO CYTOTOXICITY OF CARVEDILOL ON HUMAN TUMOR CELL LINES | |
|---|---|
| Cell line | $ED_{50}$ (μg/ml) |
| PTC (colon) | 7.0 ± 0.7 |
| B16F10 (melanoma) | 10.5 ± 1.7 |
| PA1 (ovary) | 11.5 ± 2.1 |
| HBL100 (breast) | 29.0 ± 4.2 |
| MOLT4 (leukemia) | 12.5 ± 1.0 |
| U87.MG (glioblastoma) | 14.5 ± 2.2 |
| KB (oral) | 12.0 ± 1.8 |
| DU145 (prostate) | 9.0 ± 0.9 |
| MiaPaCa.2 (pancreas) | 33.0 ± 4.6 |
| L132 (lung) | 16.0 ± 3.1 |

EXAMPLE 2

Anti-tumor Activity of the Optically Pure Isomers of Carvedilol

The anti-tumor activity of the optically pure isomers of Carvedilol S(−) and R(+) were evaluated in a 72-hour MTT cytotoxicity assay (Mosmann T., J Immunological Methods, 65:55; 1983) as explained above. Carvedilol and its isomers were evaluated in human tumor cell lines MOLT-4 (leukemia), PTC (colon), KB (oral), L132 (lung) U87MG (glioblastoma), HBL100 (breast), B16F10 (Melanoma), MiaPaCa.2 (Pancreas) and PA-1 (ovary) in a range of concentrations. The $ED_{50}$ value (the test concentration which causes 50% cytotoxicity) as calculated graphically was used to compare the relative cytotoxic potential of Carvedilol and its isomers. As shown in Table 2, the active isomers have retained the cytotoxic potential of the parent compound Carvedilol. This shows that the optically pure isomers of Carvedilol are potential anti-cancer agents with the advantage of reduced compounded toxicities associated with the parent compound.

TABLE 2

$ED_{50}$ values for Carvedilol isomers

| | $ED_{50}$ (ug/ml) | | |
|---|---|---|---|
| Cell line (cancer type) | CARVEDILOL | S(−) isomer | R(+) isomer |
| MOLT-4 (Leukemia) | 12.5 ± 1.0 | 17.0 ± 2.5 | 12.0 ± 1.6 |
| PA-1 (Ovary) | 11.5 ± 2.1 | 13.0 ± 1.3 | 10.0 ± 1.5 |
| PTC (Colon) | 7.0 ± 0.7 | 7.5 ± 0.4 | 7.0 ± 0.4 |
| KB (Oral) | 12.0 ± 1.8 | 19.0 ± 3.4 | 12.0 ± 2.6 |
| L132 (Lung) | 16.0 ± 3.1 | 22.6 ± 3.8 | 16.0 ± 3.1 |
| B16.F10 (Melanoma) | 10.5 ± 1.7 | 11.4 ± 2.1 | 10.5 ± 1.6 |
| MiaPaCa.2 (Pancreas) | 33.0 ± 4.6 | 33.0 ± 3.9 | 27.0 ± 2.7 |
| U87MG (Glioblastoma) | 14.5 ± 2.2 | 18.5 ± 2.1 | 14.5 ± 2.9 |
| HBL100 (Breast) | 29.0 ± 4.2 | 33.5 ± 4.2 | 32.8 ± 3.7 |

EXAMPLE 3

Effect of Carvedilol on Epidermal Growth Factor (EGF) Dependent Proliferation in vitro The effect of Carvedilol on Epidermal growth factor (EGF) dependent proliferation was determined by the quantitation of percent viable cells in sera free conditions in vitro.

Figure 2:
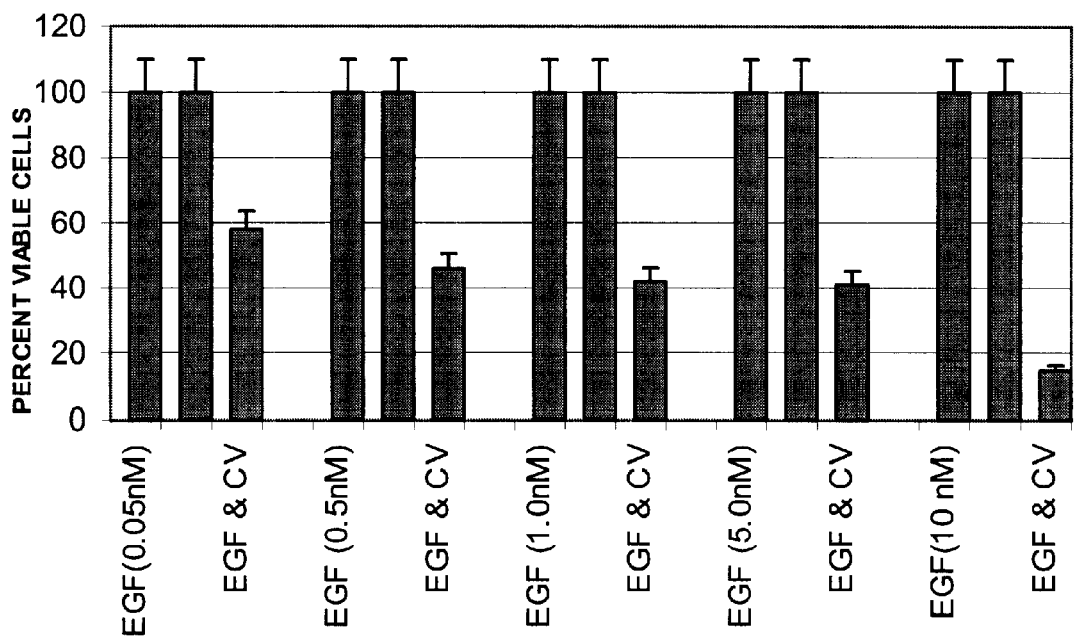
FIG. 2 shows effect of carvedilol on EGF dependent proliferation in pancreactic cancer cells (MiaPaCa2) in vitro.

Briefly, 10000 human pancreatic cancer cells (MiaPaCa2) were seeded per well in a 96-well culture plate in DMEM containing 5% FCS. All experiments were carried out in triplicates at 37° C. in a $CO_2$ incubator. The cells were incubated for a period of 12 hours, washed once with PBS and the medium was changed to DMEM without Fetal calf serum (FCS). Carvedilol was dissolved in 1% DMSO in DMEM. The cells were incubated with Carvedilol at a concentration of 20 ug/l for a period of 16 hours. The untreated control cells were treated with 1% DMSO in DMEM. The cells were washed with PBS and incubated with varying concentrations of EGF in DMEM without FCS for a period of 48 hours. The percent viable cells in absence and presence of Carvedilol was determined in an MTT assay in vitro. As shown in FIG. 2, Carvedilol inhibits the EGF dependent proliferation in pancreatic cancer cells in a dose dependent manner in vitro.

EXAMPLE 4

Figure 3:
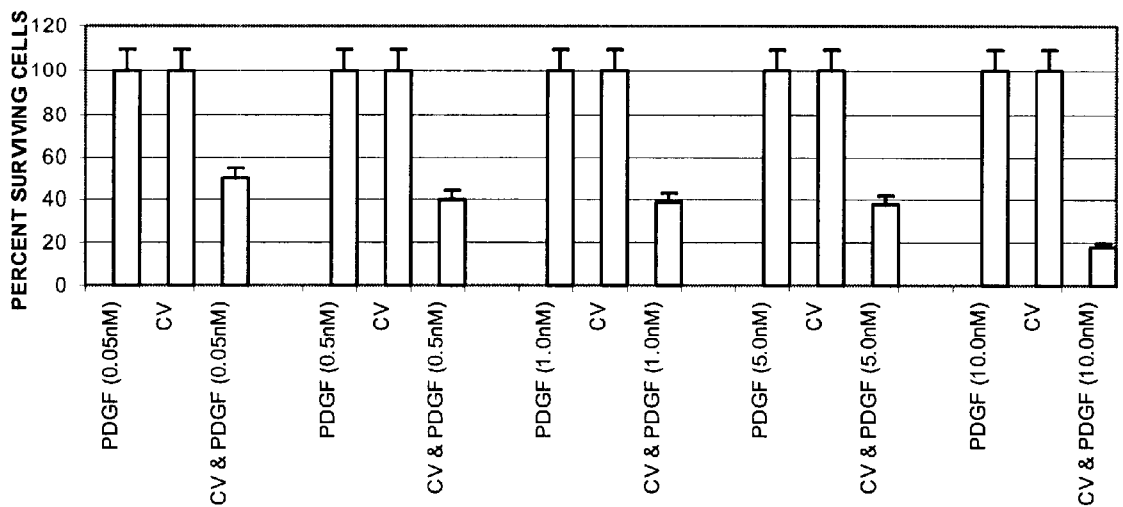
FIG. 3 shows effect of carvedilol on PDGF dependent proliferation in pancreatic cancer cells (MiaPaCa2) in vitro.

Effect of Carvedilol on Platelet Derived Growth Factor (PDGF) Dependent Proliferation in vitro The effect of Carvedilol on Platelet derived growth factor (PDGF) dependent proliferation was determined by the quantitation of percent viable cells in sera free conditions in vitro. Briefly, 10000 human pancreatic cancer cells (MiaPaCa2) were seeded per well in a 96-well culture plate in DMEM containing 5% fetal calf serum (FCS). All experiments were carried out in triplicates at 37° C. in a $CO_2$ incubator. The cells were incubated for a period of 12 hours, washed once with PBS and the medium was changed to DMEM without FCS. Carvedilol was dissolved in 1% DMSO in DMEM The cells were incubated with Carvedilol at a concentration of 20 ug/ml for a period of 16 hours. The untreated control cells were treated with 1% DMSO in DMEM. The cells were washed with PBS, to remove Carvedilol and incubated with varying concentrations of PDGF in DMEM without FCS for a period of 48 hours. The percent viable cells in absence and presence of Carvedilol was determined in an MTT assay in vitro. FIG. 3 shows that Carvedilol inhibits the PDGF dependent proliferation in human pancreatic cancer cells in a dose dependent manner in vitro.

EXAMPLE 5

Effect of Intracellular Blocking of Protein Kinase C (PKC) on the Cytotoxicity of Carvedilol in vitro The effect of PKC activation, on the cytotoxicity of Carvedilol was studied by the intracellular blocking of PKC, in cytotoxicity abrogation assays.

Briefly, 10000 human pancreatic cancer cells (MiaPaCa2) were seeded per well in a 96-well culture plate in DMEM containing 5% FCS. All experiments were carried out in triplicate at 37° C. in $CO_2$ incubator. The plates were incubated overnight to allow complete reattachment of the cells. Subsequently, the medium was replaced with DMEM. The cells were incubated with varying concentrations of Bisindolylmaleimide, the specific inhibitor of PKC for a period of three hours. Bisindolylmaleimide was dissolved in 1% DMSO The control cells were treated with 1% DMSO. The cells were washed with PBS, and the medium was changed to fresh DMEM. Carvedilol was added to the cells preincubated with or without Bisindolylmaleimide for 48 hours. Carvedilol was added every 24 hours. The percent cytotoxicity of Carvedilol in cells preincubated with or without Bisindolylmaleimide at non toxic concentrations was calculated, and the percent abrogation in the cytotoxicity determined. Table 3 shows the data on modulation of cytotoxicity of Carvedilol in presence or absence of Bisindolylmaleimide. As seen in table 3, blocking of PKC by Bisindolylmaleimide, abrogates the cytotoxicity of Carvedilol to a significant extent, suggesting a role for it in the observed anticancer action of Carvedilol.

TABLE 3

| Concentration of Bisindolemaleimide (uM) | % Cytotoxicity of Carvedilol (20 ug/ml) |
| --- | --- |
| Nil | 50% ± 3 |
| 1.0 | 22% ± 4 |
| 2.5 | 20% ± 4 |
| 5.0 | 20% ± 5 |

EXAMPLE 6

Effect of Intracellular Blocking of PI3 Kinase on Cytotoxicity of Carvedilol in vitro The effect of PI3 kinase activation, on the cytotoxicity of Carvedilol was studied by the intracellular blocking of PI3 kinase, in cytotoxicity abrogation assays.

Briefly, 10000 human pancreatic cancer cells (MiaPaCa2) were seeded per well in a 96-well culture plate in DMEM containing 5% FCS. All experiments were carried out in triplicate at 37° C. in $CO_2$ incubator. The plates were incubated overnight to allow complete reattachment of the cells. Subsequently, the medium was replaced with DMEM. The cells were incubated with varying concentrations of Wortmannin, the specific inhibitor of PI3 kinase for a period of three hours. Wortmannin was dissolved in 0.5% DMSO. The control cells were treated with 0.5% DMSO. The cells were washed with PBS, and the medium was changed to fresh DMEM. Carvedilol was added to the cells preincubated with or without Wortamannin for 48 hours. Carvedilol was added every 24 hours. The percent cytotoxicity of Carvedilol in cells preincubated with or without Wortmannin at non toxic concentrations was calculated, and the percent abrogation in the cytotoxicity determined. Table 4 shows the data on modulation of cytotoxicity of Carvedilol in presence or absence of Wortamannin. As seen in Table 4, the blocking of the activity of PI3 kinase by Wortamannin abrogates the cytotoxicity of Carvedilol, suggesting the role of the kinase in its observed action.

TABLE 4

| Concentration of Wortamannin (nM) | % Cytotoxicity of Carvedilol (20 ug/ml) |
| --- | --- |
| Nil | 50% ± 4.5 |
| 0.5 | 22% ± 4.0 |
| 1.0 | 20% ± 3.5 |
| 1.5 | 19% ± 4.0 |
| 2.0 | 18% ± 5.0 |

EXAMPLE 7

Effect of Carvedilol on PKC Activity in vitro

Figure 4:
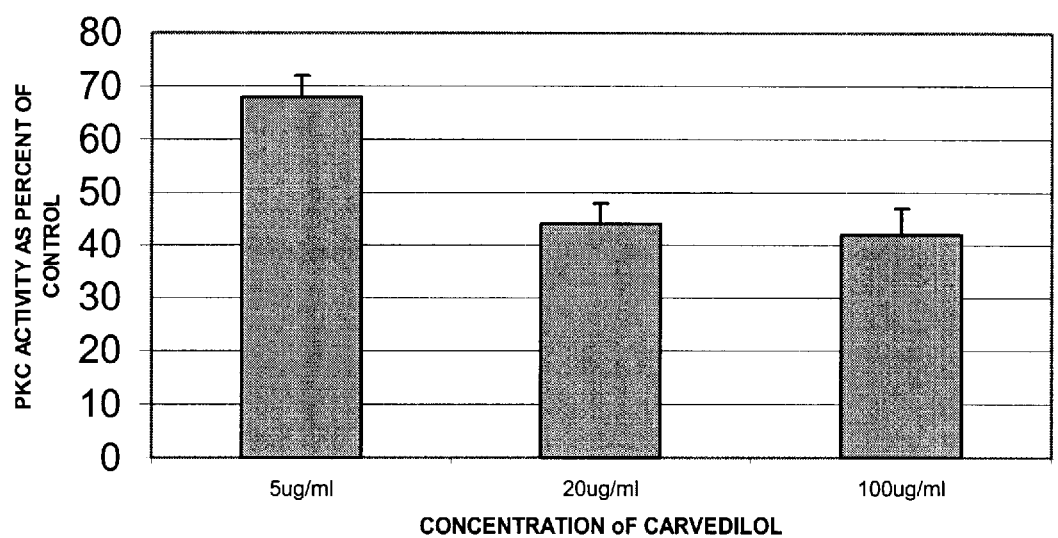
FIG. 4 shows effect of carvedilol on protein kinase C (PKC) activity in pancreatic cancer cells (MiaPaCa2) in vitro.

The effect of Carvedilol on the activity of Protein Kinase C (PKC) was quantitated by an Enyme linked immunosorbent assay (ELISA). Briefly $0.5 \times 10^6$ cells of human pancreatic cancer cells (MiaPaCa2) were plated per well in 6 well tissue culture plates in 2 ml of DMEM containing 10% Fetal calf serum. The cells were incubated overnight at 37° C. and 5% $CO_2$. The medium was changed to DMEM without serum. Carvedilol was dissolved in 1% DMSO in DMEM. The cells were incubated with Carvedilol at concentrations of 5–100 ug/ml for a period of 15 minutes at 37° C. in 5% $CO_2$. The control cells were treated with 1% DMSO in DMEM. The medium containing the Carvedilol was aspirated, and the cells were washed with Phosphate buffered saline (PBS) (50 mM, pH 7.2) twice. The cells were scraped with sterile cell scrapers, and spun at 1500 rpm for 5 minutes. The cell pellet was dissolved in 1 ml of ice cold sample preparation buffer (50 mM Tris-HCl, 50 mM 2-mercaptoethanol, 10 mM EGTA, 5 mM EDTA, 1 mM PMSF, 10 mM Benzamidine, pH 7.5). The cell pellets were sonicated four to five times each with time intervals of 5–10 seconds. The cells were centrifuged at 100,000×g for a period of 60 minutes at 4° C. The supernatant was aspirated from each set of experiments. The reaction mixture for quantitation of the PKC activity contained 25 mM Tris-HCl (pH7.0), 3 mM Mgc12, 0.1 mM ATP, 2 mM CaCl2, 50 ug/ml Phosphatidylserine, 0.5 mM EDTA, 1 mM EGTA, and 5 mM 2 mercaptoethanol. The lysates from the cells not treated with Carvedilol were the control experiments. The reaction mixture was preincubated for 5 minutes at 25° C. 50 ug of the cell lysate from different experiments was added to the individual reaction mix and added to microtitre plates coated with substrate for PKC. The plates were incubated for 15 minutes at 25° C. in a water bath. The PKC mediated reaction was stopped by the addition of 100 ul of stop solution. The plates were washed 5 times with the wash solution, and 100 ul of the biotinylated antibody to the phosphorylated substrate was added per well. The plates were incubated at 25° C. for 60 minutes. The plates were washed 5 times and 100 ul of peroxidase conjugated streptavidin was added to each well. The plates were incubated at 25° C. for 60 minutes. The plates were washed five times and 100 ul of substrate was added to each well. The plates were incubated at 25° C. for 3–4 minutes, and the reaction was stopped by the addition of stop solution. The optical density was read at 492 nM, and the PKC activity expressed as percent of that in control cells. FIG. 4 shows the data on modulation of PKC activity by Carvedilol in pancreatic cancer cells as seen below, Carvedilol inhibits the PKC activity in a dose dependent manner in human pancreatic cancer cells in vitro.

EXAMPLE 8

Effect of Carvedilol on Activity of Cyclooxygenase 2 Enzyme $1×10^6$ human pancreatic cancer cells (MiaPaCa2) were plated in 6 well plates in RPMI containing 10% FCS. The cells were incubated for a period of 24 hours at 37° C. in 5% $CO_2$. The medium was changed to DMEM without serum. Carvedilol was dissolved in 1% DMSO in DMEM. The cells were incubated with Carvedilol at concentrations of 10 ug/ml and 20 ug/ml for a period of 4 hours. All experiments were carried out in duplicates. The cells not treated with Carvedilol were the control experiments. Cells were preincubated with Bisindolemaleimide (1 uM), a specific inhibitor of PKC for 4 hours. The medium was aspirated to remove Bisindolemaleimide, and the cells were washed twice with PBS. These cells were treated with Carvedilol at 10 ug/ml and 20 ug/ml. The medium was removed in all wells after Carvedilol treatment, and 1 ml of fresh medium containing Arachidonic acid (20 uM) was added to the wells. The cells were incubated at 37° C. for one hour. Indomethacin at a concentration of 10 ug/ml was added to the wells to block the COX enzyme. The intracellular and secreted levels of PGE2 were quantitated in cells treated with Carvedilol. The cells were lysed (2.5% dodecyltrimethylammonium) and incubated for 10 minutes at room temperature. The cell lysates were transferred to microtitre plate coated with goat anti mouse Ig coated plate. 50 microliter of PGE2 standards ranging from 2.5 to 320 pg/ml were added to the microtitre plate in duplicates. 50 microliter of mouse anti PGE2 and 50 microliter of PGE2 conjugated peroxidase was added to the wells. The plate was covered and incubated at room temperature for one hour on a microtitre plate shaker. The wells were aspirated and washed 4 times with suitable was buffer. 150 microlire of enzyme substrate was added to all the wells. The plate was incubated for a period of 30 minutes and the colour development was stopped by the addition of 1N sulphuric acid. The OD was read at 450 nM.

Figure 5:
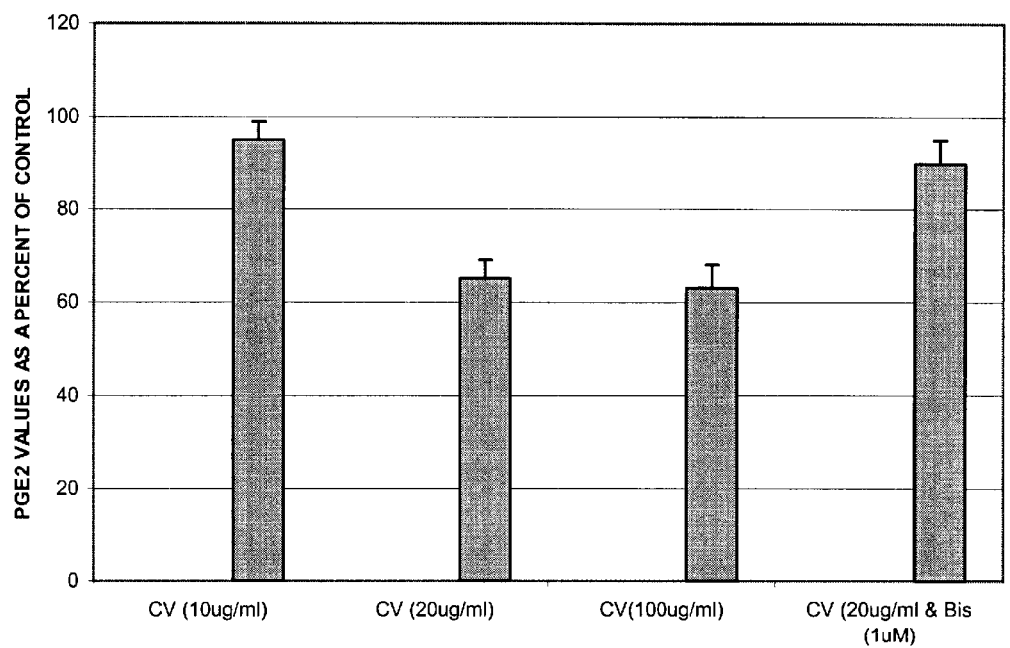
FIG. 5 shows effect of carvedilol on COX2 enzyme activity in pancreatic cancer cells (MiaPaCa2) in vitro.

The levels of secreted and intracellular PGE2 were quantitated in the cells treated with Carvedilol and compared with that in untreated cells. The levels of secreted and intracellular PGE2 were quantitated in cells treated with or without bisindolemaleimide. As shown in FIG. 5, Carvedilol inhibits the COX2 activity in pancreatic cancer cells in vitro. The blocking of PKC by its specific inhibitor bisindolemaleimide, abrogates the effect of Carvedilol on COX 2 activity, suggesting that it may be PKC mediated.

EXAMPLE 9

The Antitumor Activity of Carvedilol on Melanoma Tumor Xenografts Grown in Nude Mice The in vivo antitumor activity of Carvedilol has been demonstrated using the B16F10 melanoma xenograft model. Melanoma tumor xenografts were initiated in Balb/c athymic mice by subcutaneous inoculation of a single cell suspension of B16F10 cells ($10×10^6$ cells/100 µL). The tumor-bearing mice were divided into three groups of 4 animals each. Carvedilol was prepared at a concentration of 1.2 mg/ml so as to deliver a dose of 300 µg per 250 µl and 600 µg per 500 µl by Oral gavage once a day. The third group served as control. Treatment with Carvedilol was initiated on day 8. The anti-tumor activity was monitored by measuring the tumors using a vernier caliper every fourth day and calculating volumes using the formula $0.4×W^2×L$ (W= smaller dia, L=larger dia,).

Figure 6:
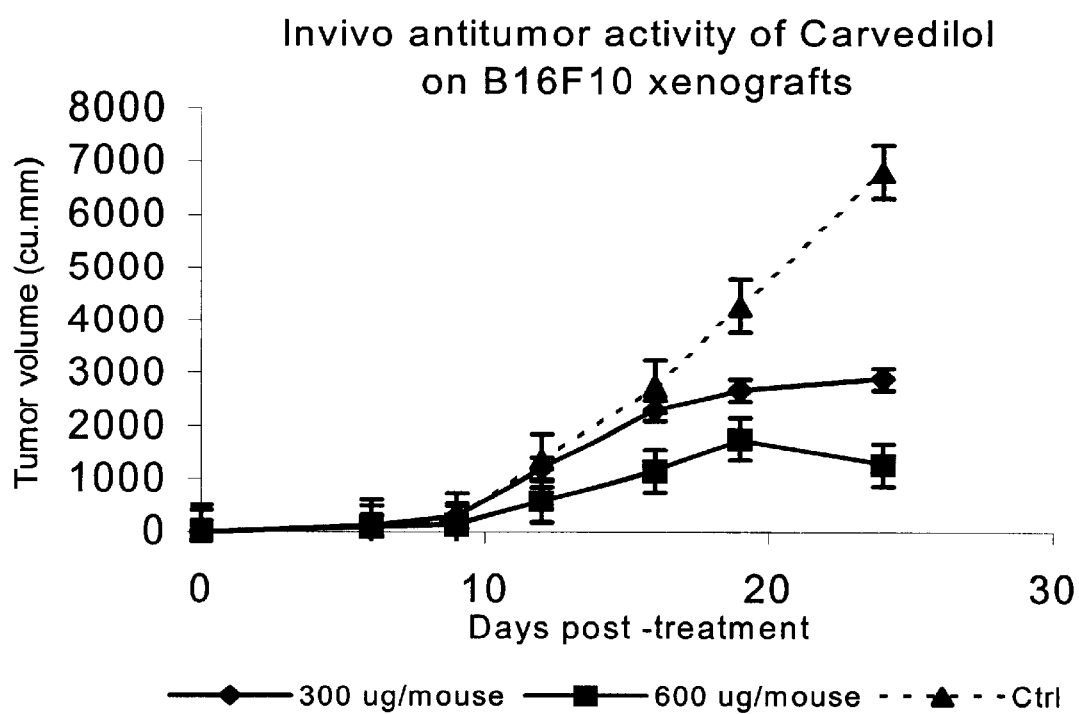
FIG. 6 shows in vivo antitumor activity of carvedilol on B16F10 xenografts.

FIG. 6 shows the pattern of tumor growth in treated and control tumor-bearing animals and shows the delayed tumor growth and tumor regression in both the doses of carvedilol treated mice. On Day 19, treatment with Carvedilol (300 ug/day) caused 37.3% tumor inhibition and Carvedilol (600 ug/day) caused 59.1% tumor inhibition based on tumor volumes compared with untreated controls.

EXAMPLE 10

Acute Toxicity of Carvedilol in Mice

Carvedilol is used clinically in doses ranging between 6.5 mg/day to 100 mg/day in humans. Since most anti-cancer drugs have very narrow therapeutic indices we determined the therapeutic index of carvedilol in mice. Acute toxicity studies were performed using two preferred routes of administration: intravenous and oral administration. A range of doses between 0.1 to 10 mg was administered in mice using either the intravenous or oral routes and the animals were observed for two weeks. In Swiss albino mice, weighing 25 grams, lethal dose (6 mg oral, 1.25 mg i.v.) and safe dose (3 mg oral, 0.15 mg i.v.) was observed. We tested the in vivo antitumor activity of Carvedilol in mice using oral doses that were $^{1}/_{10}{}^{th}$ (300 ug/day) and $^{1}/_{5}{}^{th}$ (600 ug/day) of the safe dose and have shown therapeutic efficacy (see Example 2) with a wide therapeutic index.

What is claimed is:

1. A method for treating cancer or a tumor comprising administering an effective amount of carvedilol, an S(−) or R(+) isomer of carvedilol or a mixture thereof to a patient in need thereof wherein the cancer or tumor is of the colon, ovary, breast, prostate, pancreas, or lung, or is melanoma, glioblastoma, oral cancer, or leukemia.

2. A method for inhibiting epidermal growth factor dependent proliferation in cancer cells comprising administering an effective amount of carvedilol, an S(−) or R(+) isomer of carvedilol or a mixture thereof to a patient in need thereof.

3. A method for inhibiting epidermal growth factor dependent proliferation in cancer cells comprising incubating with or adding to the cancer cells an effective amount of carvedilol, an S(−) or R(+) isomer of carvedilol or a mixture thereof in vitro, or administering said carvedilol, an (S)(−) or R(+) isomer of carvedilol, or a mixture thereof to a patient in need thereof.

4. A method for inhibiting platelet derived growth factor dependent proliferation in cancer cells comprising administering to a patient in need thereof an effective amount of carvedilol, an S(−) or R(+) isomer of carvedilol or a mixture thereof.

5. A method of according to claim 1 wherein the carvedilolan, an S(−) or R(+) isomer of carvedilol or a mixture thereof is administered in combination with a pharmaceutically acceptable excipient, additive, carrier, diluent, solvent, filler, lubricant, binder or stabilizer.

6. A method according to claim 1 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

7. A method of according to claim 2 wherein the carvedilol, an S(−) or R(+) isomer of carvedilol or a mixture thereof is administered in combination with a pharmaceutically acceptable excipient, additive, carrier, diluent, solvent, filler, lubricant, binder or stabilizer.

8. A method according to claim 2 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

9. A method of according to claim 3 wherein the carvedilol, an S(−) or R(+) isomer of carvedilol or a mixture thereof is administered in combination with a pharmaceutically acceptable excipient, additive, carrier, diluent, solvent, filler, lubricant, binder or stabilizer.

10. A method according to claim 3 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

11. A method of according to claim 4 wherein the carvedilol, an S(−) or R(+) isomer of carvedilol or a mixture thereof is administered in combination with a pharmaceutically acceptable excipient, additive, carrier, diluent, solvent, filler, lubricant, binder or stabilizer.

12. A method according to claim 4 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

13. A method of inhibiting epidermal growth factor dependent proliferation in cancer cells comprising administering an effective amount of carvedilol, an S(−) or R(+) isomer of carvedilol or a mixture thereof to cancer cells in vitro.

14. A method of treating cancer by inhibiting epidermal growth factor dependent proliferation in cancer cells comprising administering an effective amount of carvedilol, an S(−) or R(+) isomer of carvedilol or a mixture thereof to a patient in need thereof.

15. A method according to claim 13 wherein the carvedilol, an S(−) or R(+) isomer of carvedilol or a mixture thereof is administered in combination with a pharmaceutically acceptable excipient, additive, carrier, diluent, solvent, filler, lubricant, binder or stabilizer.

16. A method according to claim 13 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

17. A method of inhibiting platelet derived growth factor dependent proliferation in cancer cells comprising administering an effective amount of carvedilol, an S(−) or R(+) isomer of carvedilol or a mixture thereof to cancer cells in vitro.

18. A method of treating cancer by inhibiting platelet derived growth factor dependent proliferation in cancer cells comprising administering an effective amount of carvedilol, an S(−) or R(+) isomer of carvedilol or a mixture thereof to a patient in need thereof.

19. A method of according to claim 17 wherein the carvedilol, an S(−) or R(+) isomer of carvedilol or a mixture thereof is administered in combination with a pharmaceutically acceptable excipient, additive, carrier, diluent, solvent, filler, lubricant, binder or stablizer.

20. A method according to claim 17 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

21. A method of inhibiting intracellular Protein Kinase C activity in cancer cells comprising administering an effective amount of carvedilol, an S(−) or R(+) isomer of carvedilol or a mixture thereof to cancer cells in vitro.

22. A method of treating cancer by intracellular inhibition of Protein Kinase C activity in cancer cells comprising administering an effective amount of carvedilol, an S(−) or R(+) isomer of carvedilol or a mixture thereof administered to a patient in need thereof.

23. A method of according to claim 21 wherein the carvedilol, an S(−) or R(+) isomer of carvedilol or a mixture thereof is administered in combination with a pharmaceutically acceptable excipient, additive, carrier, diluent, solvent, filler, lubricant, binder or stabilizer.

24. A method according to claim 21 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

25. A method of blocking intracellular PI3 Kinase in cancer cells comprising administering an effective amount of carvedilol, an S(−) or R(+) isomer of carvedilol or a mixture thereof to cancer cells in vitro.

26. A method of treating cancer by intracellular blocking of PI3 Kinase in cancer cells comprising administering an effective amount of carvedilol, an S(−) or R(+) isomer of carvedilol or a mixture thereof a patient in need thereof.

27. A method of according to claim 25 wherein the carvedilol, an S(−) or R(+) isomer of carvedilol or a mixture thereof is administered in combination with a pharmaceutically acceptable excipient, additive carrier, diluent, solvent, filler, lubricant, binder or stabilizer.

28. A method according to claim 25 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

29. A method of inhibiting cyclooxygenase 2 enzyme in cancer cells comprising administering an effective amount of carvedilol, an S(−) or R(+) isomer of carvedilol or a mixture thereof to cancer cells in vitro.

30. A method of treating cancer by inhibiting cyclooxygenase 2 enzyme in cancer cells comprising administering an effective amount of carvedilol, an S(−) or R(+) isomer of carvedilol or a mixture thereof to a patient in need thereof.

31. A method of according to claim 29 wherein the carvedilol, an S(−) or R(+) isomer of carvedilol or a mixture thereof is administered in combination with a pharmaceutically acceptable excipient, additive, carrier, diluent, solvent, filler, lubricant, binder or stabilizer.

32. A method according to claim 29 wherein the carvedilol, an S(−) or R(+) isomer of carvedilol or a mixture thereof is administered in the form of a tablet, lozenge, capsule, powder, aqueous or oily suspension, syrup, elixir, implant or aqueous solution.

33. A method for treating cancer or a tumor comprising administering an effective amount of carvedilol, an (S)(−) or R(+) isomer of carvedilol, or a mixture thereof to a patient in need thereof, wherein said treatment comprises a) inhibiting epidermal growth factor dependent proliferation in cancer or tumor cells; b) inhibiting platelet derived growth factor dependent proliferation in cancer or tumor cells; c) inhibiting intracellular inhibition of Protein Kinase C activity in cancer or tumor cells; d) intracellularly blocking P13 Kinase in cancer or tumor cells; or e) inhibiting cyclooxygenase 2 enzyme in cancer or tumor cells.

\* \* \* \* \*